United States Patent
Worley et al.

(10) Patent No.: US 7,993,351 B2
(45) Date of Patent: Aug. 9, 2011

(54) TELESCOPIC INTRODUCER WITH A COMPOUND CURVATURE FOR INDUCING ALIGNMENT AND METHOD OF USING THE SAME

(75) Inventors: Seth J. Worley, Lancaster, PA (US); Paul Kurth, Rancho Palos Verdes, CA (US)

(73) Assignee: Pressure Products Medical Supplies, Inc., Grand Teton, WY (US)

( * ) Notice: Subject to any disclaimer, the term of this patent is extended or adjusted under 35 U.S.C. 154(b) by 2638 days.

(21) Appl. No.: 10/202,158

(22) Filed: Jul. 24, 2002

(65) Prior Publication Data

US 2004/0019359 A1  Jan. 29, 2004

(51) Int. Cl.
*A61B 19/00* (2006.01)
*A61M 25/00* (2006.01)

(52) U.S. Cl. ........ 606/129; 600/585; 604/264; 604/523; 604/525; 604/532; 606/108; 606/191; 606/192; 606/194

(58) Field of Classification Search .................. 606/129, 606/108, 191; 604/264, 523, 525, 532; 600/585
See application file for complete search history.

(56) References Cited

U.S. PATENT DOCUMENTS

| | | | | |
|---|---|---|---|---|
| 5,669,882 A * | 9/1997 | Pyles | ........................ | 604/170.03 |
| 5,814,029 A * | 9/1998 | Hassett | ......................... | 604/528 |
| 5,817,046 A | 10/1998 | Glickman | | |
| 6,562,049 B1 | 5/2003 | Norlander et al. | | |
| 6,755,812 B2 * | 6/2004 | Peterson et al. | ............... | 604/528 |

* cited by examiner

*Primary Examiner* — Vy Q Bui
(74) *Attorney, Agent, or Firm* — Daniel L. Dawes; Marcus C. Dawes

(57) ABSTRACT

An introducer system for implantation of pacemaker leads into the venous system of the human heart through the coronary sinus is comprised of a flexible, elongate, outer elongate element having a first shape or bias along a portion. The first shape on the outer element may be prebiased or may be initially straight and subsequently biased once deployed in the body chamber. A flexible, elongate, telescopic inner elongate element has a second shape or bias on its distal portion and has the first shape or bias on a more proximal portion. The inner elongate element is telescopically disposed in the outer sheath. The outer and inner elongate elements are rotatable with respect to each other, such that when the inner elongate element is distally extended from the outer sheath, there exists an angular orientation between the inner and outer sheaths which is congruent, when there is at least partial alignment between the distal portion of the outer elongate element and the more proximal portion of the inner sheath, both having the first shape or bias. This results in the rotation of the distal second shape or curve of the inner elongate element into a predetermined three dimensional location.

29 Claims, 11 Drawing Sheets

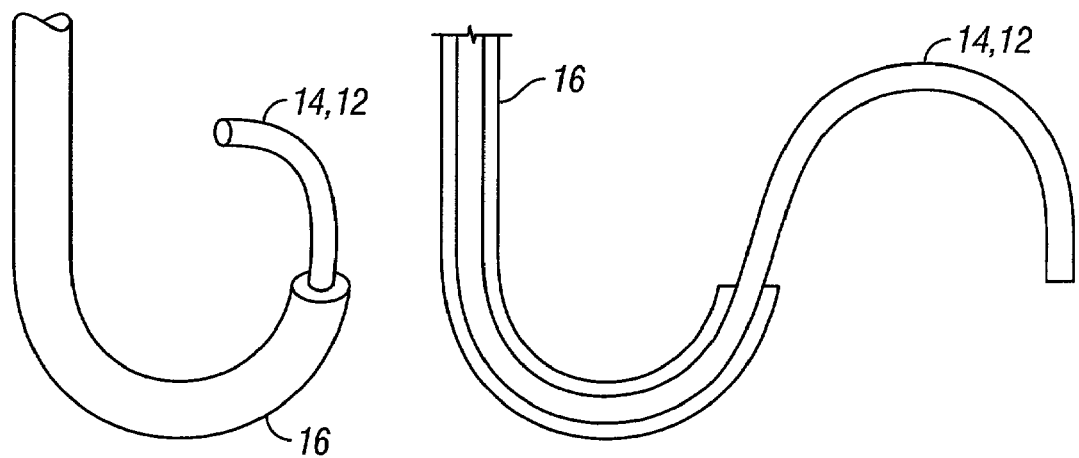
FIG. 1C  FIG. 1E
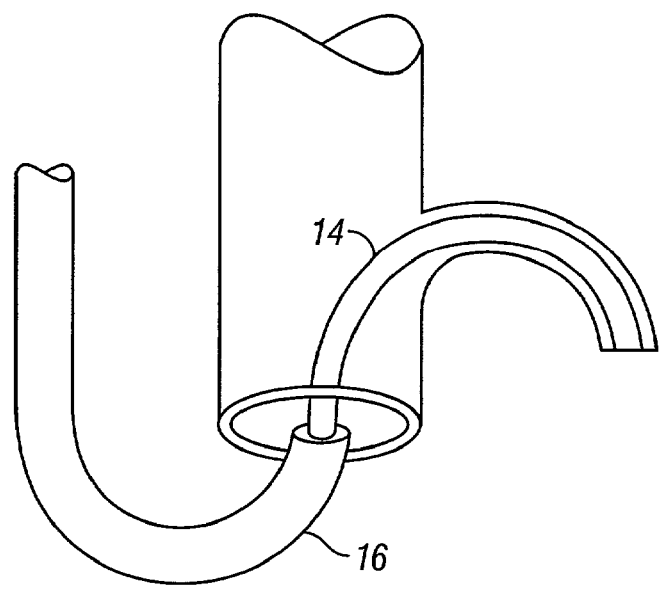
FIG. 1D

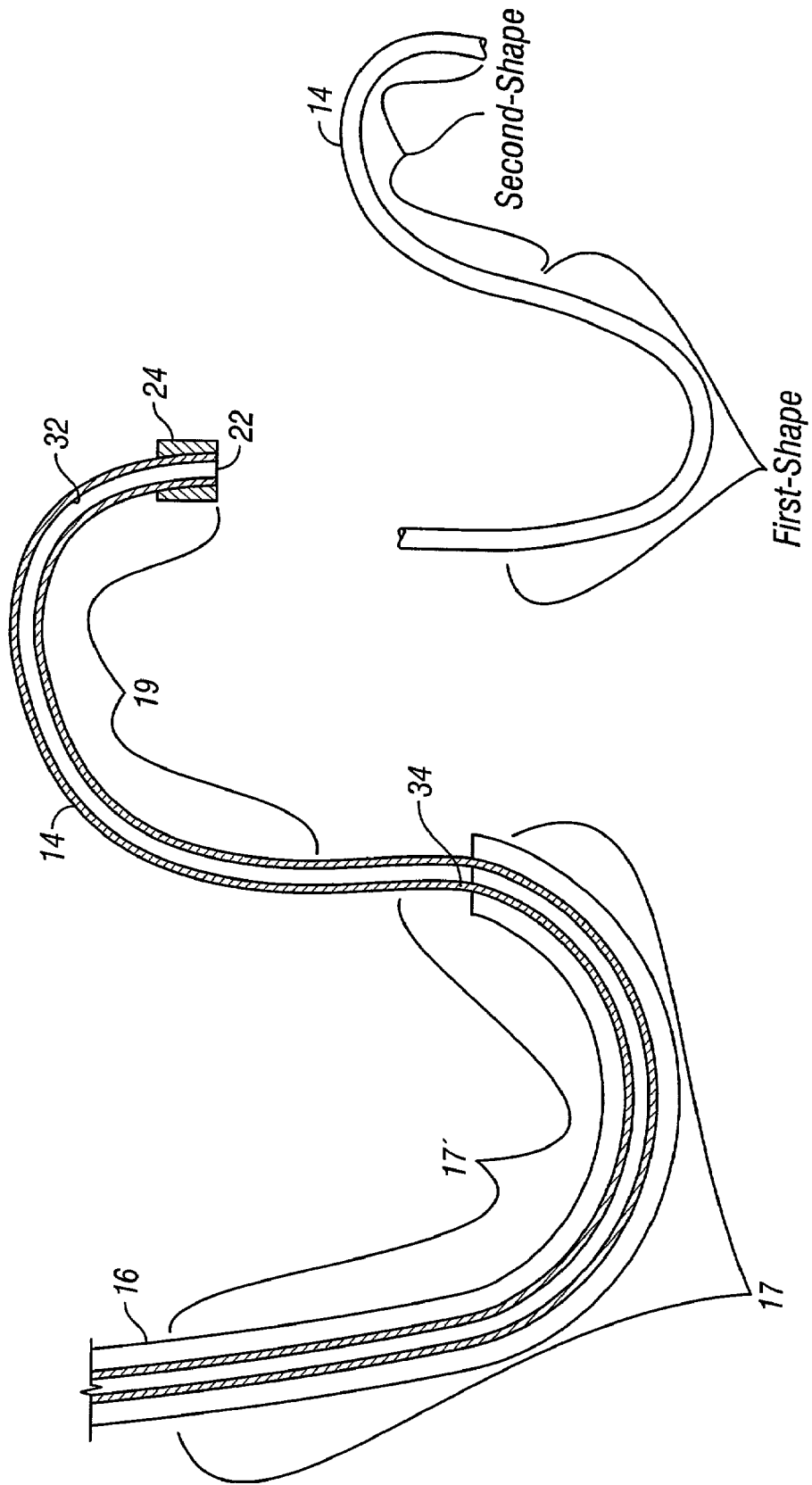

TELESCOPIC INTRODUCER WITH A COMPOUND CURVATURE FOR INDUCING ALIGNMENT AND METHOD OF USING THE SAME

BACKGROUND OF THE INVENTION

1. Field of the Invention

The invention relates to the field of catheters, guides, sheaths and introducers, which are utilized in a human heart. More particularly, this invention relates to a telescopic elongate cardiac instrument whose telescopic sections are made to align with each other.

2. Description of the Prior Art

The coronary sinus is the largest cardiac vein and serves as a conduit for access to various locations within the heart. Depending on the depth of insertion of the medical device into the coronary sinus, both the left and right atria and the left and right ventricles of the heart can be analyzed. However, introduction of a medical device into the ostium of the coronary sinus is quite difficult as a result of the structure of the heart, the difficulty in locating the coronary sinus using conventional medical technology and the constantly changing shape of the heart while beating as well as the altered anatomy of the heart with cardiomyopathy.

The anatomy of the coronary sinus branch vein presents novel problems for cannulation and pacemaker insertion. During pacemaker implantation the delivery system must be steerable to properly locate and insert itself into the ostium of the coronary sinus. Thereafter, the delivery device must have the ability to be steered through a highly branched vasculature to smaller and smaller vessels, yet it must not be so stiff or biased to be traumatic to the vessels. After implantation the delivery system must then leave in place a highly flexible, poorly steerable pacemaker lead.

Two approaches are commonly used for placement of a medical device within the coronary sinus, an inferior approach from below the heart, and a superior approach from above the heart. In the superior approach, the device is advanced through either the right or left cephalic or right or left subclavian vein through the superior vena cava into the right atrium until it is directed toward the coronary sinus. In the inferior approach, the device is generally advanced through the femoral vein through the inferior vena cava into the right atrium. The tip of the device is then directed toward the ostium of the coronary sinus. The superior approach is the preferred approach and is the approach for which the introducer of the present invention is optimized.

Telescopic catheters are well known and applied to a variety of arterial operations, but never before into the venous system. Typically, one use for such catheters is in the placement of angioplasty balloons in heart arteries. The following United States patents disclosed various forms of dilatation catheters: U.S. Pat. Nos. 3,435,426; 4,271,839; 4,323,071 and 4,338,942. The use of a guiding catheter having a distal tip that can be shaped to facilitate positioning or guiding a catheter into a selected coronary blood vessel is thus well known. Successful angioplasty requires that the balloon of a dilatation catheter be positioned within a stenosis. The more severe the stenosis, the more pressure required to position the dilatation catheter within it. Although very few stenoses within the main coronary artery are so severe as to be impenetrable by a balloon catheter, about 30% of stenoses located in the left circumflex artery cannot be treated with angioplasty. Such is the case because transmission of axial force to the distal end of the catheter from the proximal end is impeded by presence of a sharp bend where the catheter shaft traverses the intersection of the circumflex artery with the main artery.

Thus telescopic catheters have been devised as shown in U.S. Pat. No. 4,616,652 for introducing guide for a balloon catheter. The guide is composed of three parts that are relatively axially movable in telescoping relation to one another. The inner-most part is formed of wire the distal end of which can be selectively deformed to facilitate the manipulation of the distal end through blood vessel intersections. The center or intermediate part, which has a central lumen in which the wire is telescoped, has a tapered distal end and is formed of material possessing sufficient rigidity to be advanced along the wire after the wire is in place, and sufficient flexibility to conform to the wire configuration. The outer part telescopes on to the exterior of the intermediate part. The outer part defines a passage having an inside diameter that is large enough to afford entry of a balloon catheter therethrough. The outside diameter of the intermediate part is less than the inside diameter of the passage so that when the wire and intermediate part are positioned, the outer tube can be advanced therealong.

Thus the telescopic introducer for a dilatation catheter has sufficient flexibility to be manipulated around irregular paths, such as occur within the intersection between the main artery and the left circumflex artery, but has sufficient stiffness or rigidity that it can be moved to a position adjacent a stenosis to be treated by angioplasty. This object is effected by providing an introducer composed of three relatively axially movable parts which are so arranged that the clinician can individually control the relative axial position of each of the parts. The guide wire contained within the innermost guide controls the direction of the intermediate telescoping introducer. The introducers by themselves are not capable of negotiating the branch vessels of the coronary arteries, but instead rely on the navigation of the wire to control the direction for subsequent guides to follow.

Generally in the arterial system shaped sheaths are not used, but sheaths and catheters are generally placed using a guidewire. The reason for this is that in the high pressure arterial system there is a high probability of the existence of plaque on the artery walls. Any undue disturbance risks the dislodgment of that plaque with the possibility of a resulting heart attack or stroke. However, in the low pressure venous system plaque is generally not present and the interior vessel walls are smooth. Thus, while a guidewire can also be used in the venous system, the possibility also exists for the use of shaped sheaths, introducers and catheters which can be steered. To be steered such shaped sheaths, introducers and catheters must be torqueable or rotatable from their proximal end. It is desirable then to have both a radially flexible sheath, introducer and catheter to avoid trauma to the vessel walls and to more easily track in a tortuous or highly branched venous system, while at the same time to be shaped and torqueable. Generally, to be torqueable and radially flexible at the same time meant that the sheath, introducer and catheter had to include a braided reinforcement in or on it. However, a braided sheath, introducer and catheter means greater expense in fabrication of the sheath, introducer and catheter as well as a larger diameter of the sheath, introducer and catheter or a smaller inner diameter of any lumen in the sheath, introducer or catheter.

One prior art approach has been that shown in U.S. Pat. No. 6,185,449 in which a braidless catheter is combined with a solid inner guide 60. While the catheter is thus not torqueable, the inner guide 60 is inserted in a lumen defined within the catheter and the inner guide 60 is torsionally stiff enough to be torqueable. The catheter is hopefully rotated when the inner guide 60 is rotated. However, in this prior art case the inner guide 60 is rendered torqueable simply by having a sufficiently large enough diameter that it is rendered torsionally stiff given the material from which it is made. There is nothing in the structure of inner guide 60 which renders it torsionally stiff. Such a limitation of the diameter of inner guide 60, then limits the size of the catheters with which it is used to those having larger diameters and particularly larger diameter lumens in them to accept the larger diameter inner guide 60. Venous coronary sinus procedures or pacemaker implantations, however, require not a distal stiffness to push through a stenosis, but a variable and controllable distal flexibility or softness torque control as well as specific distal curves.

However, shaped introducers whose shape has been optimized to access the coronary sinus have been found to have the wrong or an ill-adapted orientation or direction for any telescopic portion extending therethrough to access the venous system of the heart. In other words, if an inner telescopic guide, core or introducer is biased or shaped, it will assume the same or similar planar orientation assumed by the outer or guiding introducer giving access to the coronary sinus, thus the inner telescopic guide or introducer always has an ill-adapted orientation or direction for the cardiac branch venous system. When the distal shaped end of the inner telescoping introducer emerges from the outer guide, core or introducer, the biased shaped tip of the telescoping catheter faces the plane or direction to which it is directed by the outer introducer. The shaped tip of the telescoping inner introducer is thus left facing in the opposite or wrong direction of where the tip needs to face to cannulate the coronary sinus branch veins. This then requires the physician to apply a substantial torque to the inner telescoping catheter to align the tip with the desired branch vessels, thereby making cannulation more difficult to accomplish and to maintain. The torque needed for reorienting the distal end of the telescoping inner guide, core or introducer can exceed the torsional integrity of the inner system, especially when a nonreinforced small French size introducer is used, such as in a peel away introducer.

What is needed then is some means or methodology whereby this inherent obstacle can be overcome, while still accommodating different shapes of the inner telescopic guides, cores or introducers used for the different orientations and locations of the branch veins of coronary sinus venous system.

BRIEF SUMMARY OF THE INVENTION

The invention is a telescopic introducer apparatus comprising a flexible, elongate, outer sheath, guide or introducer having a first shape or bias along a portion of its length. The outer sheath, guide or introducer is defined for the purpose of this specification and claims as an "outer elongate element". The first shape may be anywhere along the length of the outer elongate element. The shape may be straight upon entry into the vascular system and be subsequently formed at the time of final placement. A flexible, elongate, telescopic inner sheath, guide, core or introducer has a second shape or bias on its distal portion and has the first shape or bias on a more proximal portion. The inner sheath, guide core or introducer is defined for the purpose of this specification and claims as an "inner elongate element". The inner elongate element is telescopically disposed in the outer elongate element. The outer and inner elongate elements are relatively rotatable with respect to each other, such that when the inner elongate element is distally extended from the outer elongate element, there exists a mechanically or geometrically preferred angular orientation between the inner and outer elongate elements, which is congruent when there is at least partial alignment between the a portion of the outer elongate element and the more proximal portion of the inner elongate element, which two portions both have the first shape or bias. These respective portions are defined as "first-shape portions".

The alignment between the first-shape portion of the outer elongate element and the more proximal first-shape portion of the inner elongate element comprises an alignment of a longitudinal shape or bias. In another embodiment, the alignment between the first-shape portion of the outer elongate element and the more proximal first-shape portion of the inner elongate element comprises an alignment of a radial cross-sectional shape.

The telescopic inner introducer apparatus may further comprise a means for rotating a distal end of the inner elongate element from a proximal end of the inner elongate element so that the inner elongate element is steerable. The means comprises a torsionally stiff core, and wherein the inner elongate element may be torsionally flexible.

In one embodiment the inner elongate element is unreinforced. The means for rotating a distal end of the inner guide from a proximal end of the inner guide so that the inner guide is steerable comprises means for rendering the inner guide torsionally stiff, which is comprised of the braiding incorporated in or on the inner elongate element.

The inner elongate element has at least one longitudinal lumen defined therethrough adapted for injection of a fluid and at least one longitudinal lumen defined therethrough adapted for disposition of a guide wire therethrough.

The telescopic introducer apparatus further comprises a proximal sidearm communicated to the at least one longitudinal lumen and a hemostatic valve coupled to and terminating the sidearm.

The telescopic introducer apparatus further comprising a distal radio opaque section or marker on the inner elongate element and/or on the core.

In one embodiment the inner elongate element comprises a proximal flexible unbiased portion and a distal precurved portion, which has a curvature for optimally steering the inner elongate element into the coronary sinus venous system of the heart.

In another embodiment the distal precurved portion has a single radius of curvature and a distal most straight portion.

In still another embodiment the inner elongate element has a longitudinal axis and the single radius of curvature and relative length of the distal precurved portion are such that an open curve is obtained, an open curve being defined as having an angle between the direction of the longitudinal axis of the proximal portion of the inner elongate element where it joins the precurved portion and the direction of the longitudinal axis at a distal end of the precurved portion of the inner elongate element of more than 90°.

In yet another embodiment the inner elongate element as a longitudinal axis and the single radius of curvature and relative length of the distal precurved portion are such that a closed curve is obtained, a closed curve being defined as having an angle between the direction of the longitudinal axis of the proximal portion of the inner elongate element where it joins the precurved portion and the direction of the longitudinal axis at a distal end of the precurved portion of the inner elongate element of less than 90°.

In one embodiment the precurved portion of the inner elongate element comprises two curved subportions and a straight subportion therebetween of form a flattened hook. The two curved subportions comprise a proximal curved subportion having a radius of curvature of a first magnitude and a distal curved subportion having a radius of curvature of a second magnitude less than the first magnitude. The radius of curvature of the first magnitude is approximately 1 inch and where the radius of curvature of the second magnitude is approximately 0.2 to 0.3 inch.

The elongate elements may have other characteristics shapes. For example, the first-shape portion and the second-shape portion of the inner and outer elongate elements may be compound curves. The embodiments illustrated here are defined as elephant curves. More specifically, the first-shape portion and the second-shape portion of the inner and outer elongate elements lie in a common plane. The first-shape portion comprises portions having its radii of curvature lying on one side of the elongate element and the second-shape portion comprises portions having its radii of curvature lying on an opposing side of the elongate element. In the illustrated embodiment the shapes vary primarily in the nature of the second-shape portion of the inner and outer elongate elements, namely the second-shape portions are described below as a hockey stick curve, a multipurpose curve, and a hook curve.

In some embodiments the outer guide or elongate element is longitudinally openable or separable. In others the inner elongate element is longitudinally openable or separable. Embodiments are also contemplated where the outer guide and inner elongate elements are both longitudinally openable or separable.

The telescopic introducer apparatus further comprises a distal balloon, a proximal sidearm communicated to the at least one longitudinal lumen and a hemostatic valve coupled to and terminating the sidearm.

The invention can be alternatively defined as an inner telescopic introducer for use in the coronary sinus venous system comprising a flexible, elongate, nontorqueable element having a longitudinal lumen defined therein and having a first shape along proximal portion, and a second shape or bias along a distal portion. An elongate, telescopic core has the second shape or bias on its distal portion and the first shape or bias on a more proximal portion. The core is telescopically disposed in the lumen of the inner elongate element and coupled thereto. The core is structurally reinforced so that it is torsionally stiff while remaining radially flexible by virtue of a structural reinforcement in or on the core. The inner sheath and core are also relatively rotatable with respect to each other, such that when the inner sheath is distally extended from the outer elongate element, there exists an angular orientation between the inner sheath and core which is congruent when there is at least partial alignment between the first and second shape portion of the inner sheath and the first and second shape portion of the core. The core is adapted to rotationally couple with the sheath when in a congruent match so that a distal end of the sheath is rotated when a proximal end of the core is rotated. The invention is also defined as a method for using the above described introducer systems. The method comprises the step of disposing a flexible, elongate, outer elongate element which may have a portion with a first prebiased curvature or may be straight upon entry and be formed to contain a first shape bias at the time of placement into a branched body system to achieve a predetermined position of the outer elongate element in the branched body system. The branched body system may be the arterial or venous endovascular system, the lymphatic system, the endocrine system or any other network of connecting pathways in the body. A flexible, elongate, telescopic inner element is telescopically disposed into the outer elongate element. The inner elongate element has a distal second shape portion with a prebiased curvature. The inner elongate element is curved in the branched body system to match the first prebiased curvature defined in the outer elongate element. The inner elongate element is distally extended from the outer elongate element to allow the inner elongate element to assume the second prebiased curvature in the branched body system. The outer and inner elongate elements are angularly oriented with respect to each other to congruently match and come into geometric alignment with the more proximal portion of the inner elongate element having the first prebiased curvature with the portion of the outer elongate element having the first prebiased curvature so that the distal second shape portion of inner elongate element automatically rotates from its original alignment and assumes a new predetermined three dimensional position in the branched body system.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The invention can be better visualized by turning now to the following drawings wherein like elements are referenced by like numerals.

BRIEF DESCRIPTION OF THE DRAWINGS

FIG. 1*c* is a simplified cross-sectional representation of the distal curve of the inner element with the initial orientation of the distal curve with no torque or no establishment of the more proximal congruent alignment of inner and outer elements.

FIG. 1*d* is a simplified cross-sectional view showing the new rotated orientation of the distal curve of the inner elongate element after the more proximal first shape of the inner elongate element is aligned with and at least partial congruency is established with the first shape of the outer elongate element.

FIG. 1*e* is a side elevational view of the core showing a preferred shape of the core for coronary sinus branch vein cannulation.

FIG. 2*a* is a simplified diagrammatic view of another embodiment of the invention in which a torqueable reinforced telescopic inner elongate element disposed in a telescopic guide and there is no core element provided.

FIG. 2*b* shows one example of the first proximal and second distal shape of the inner elongate element.

The invention and its various embodiments can now be better understood by turning to the following detailed description of the preferred embodiments which are presented as illustrated examples of the invention defined in the claims. It is expressly understood that the invention as defined by the claims may be broader than the illustrated embodiments described below.

DETAILED DESCRIPTION OF THE PREFERRED EMBODIMENTS

Introducer system 10 of the illustrated embodiment of the invention is used for implantation of pacemaker leads or other elongate instruments or devices into the venous system of the human heart through the coronary sinus. In the illustration several predetermined shapes are employed as described below are used for that portion of introducer system 10, which delivers the elements to the coronary sinus. The term, "elements" in this specification shall mean all or any number of the components of the telescopic system, such as inner telescoping core 12, inner telescoping elongate element or guide 14, and/or an outer telescoping guide or elongate element 16. This telescopic system is commercially called the "Worley Introducer"™. This telescopic system is described in U.S. patent application for A TELESCOPIC, PEEL-AWAY INTRODUCER AND METHOD OF USING THE SAME by Worley et.al., Ser. No. 10/139,554, and U.S. patent application for AN INTRODUCER FOR ACCESSING THE CORONARY SINUS OF A HEART by Worley et.al. Ser. No. 10/139,551, which are copending with the present application, which are incorporated herein by reference. However, it must be clearly understood that any shaped delivery portion may be employed other than the "Worley Introducer"™ and be applied to sites involving other organ or body locations other than the heart. Any telescoping elongate instruments or devices include, but are not limited to, catheters, introducers, guides, dilators, surgical instruments and the like could be substituted for the examples given in the present application.

Figure 1A:
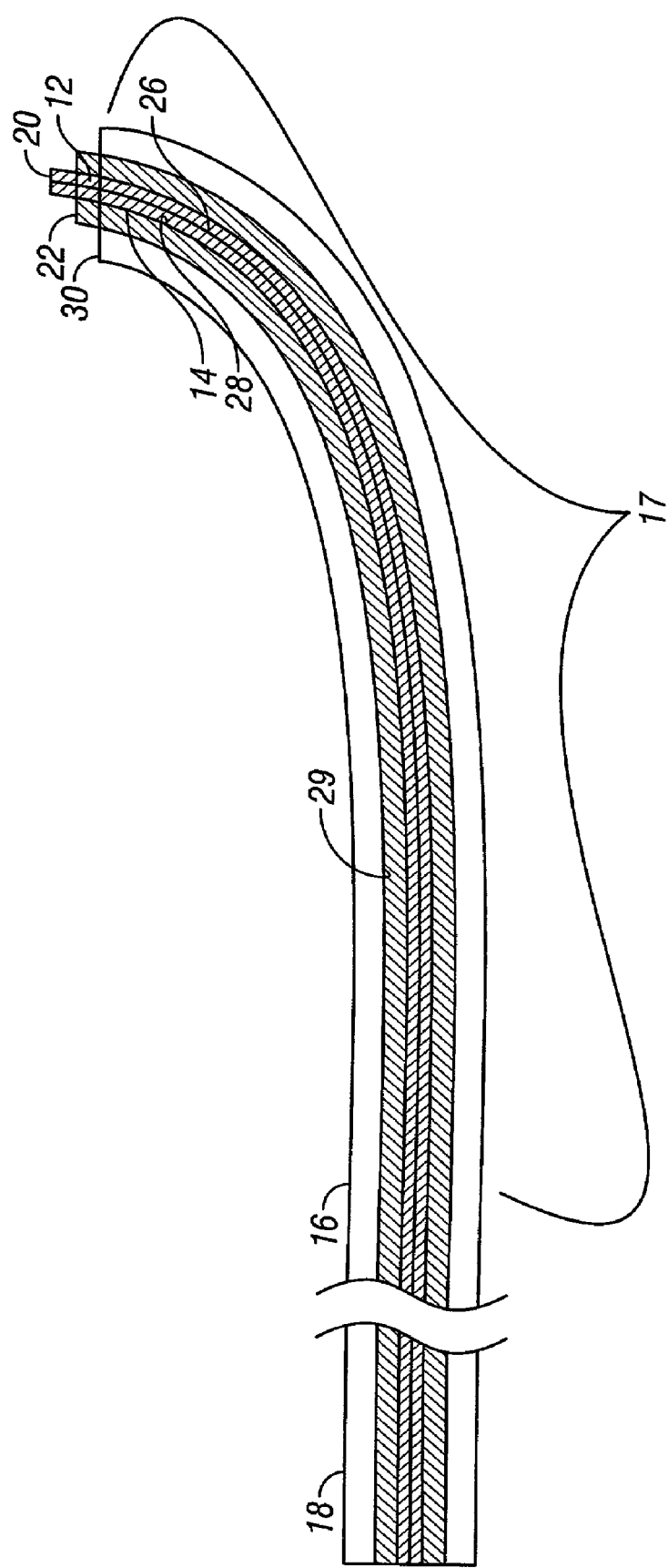
FIG. 1*a* is a simplified diagrammatic view of one embodiment of the invention in which a torqueable telescopic core is used inside an unreinforced telescopic inner elongate element disposed in an outer telescopic guide. All three components are in a position in which they are telescopically nested within each other and assume the shape of the outer telescopic guide.
Figure 1B:
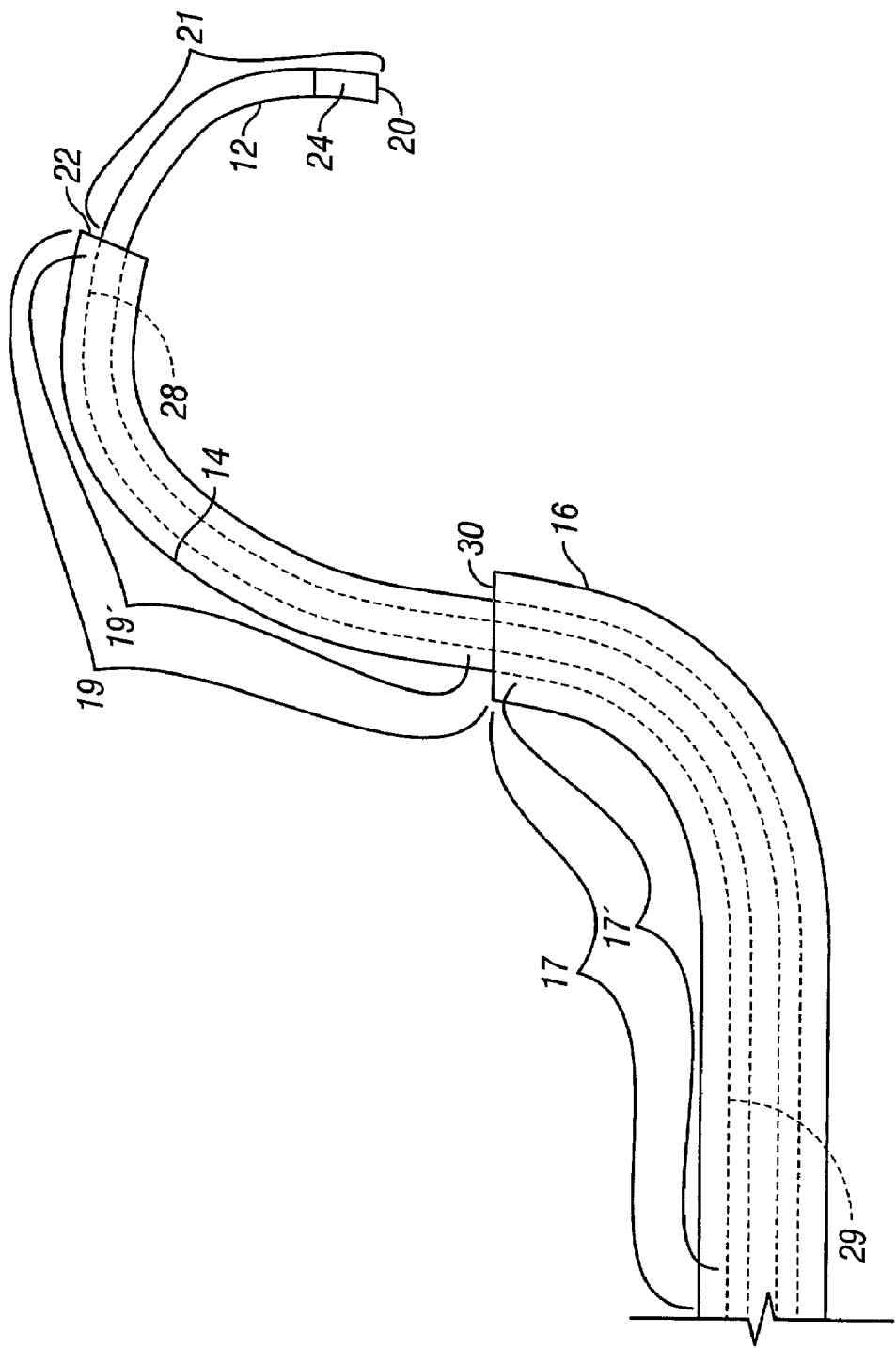
FIG. 1*b* is a simplified diagrammatic view of the embodiment of FIG. 1*a* in which the telescopic inner sheath and torqueable telescopic core are in a position in which they are telescopically distally extended out of the outer telescopic guide and assume their own biased shapes, after being inserted into the coronary sinus.

The telescopic introducer system 10 of FIGS. 1a and 1b is preferably comprised of a plurality of telescopic components, namely an inner telescoping core 12, an inner telescoping elongate element or guide 14, and an outer telescoping element 16. Outer telescoping element 16 may have a first shape or bias built into it for delivery of introducer system 10 to the heart or right atrium using a superior approach. This shape may be prebiased or may be straight and imparted to the delivery elongate element after placement. Element 14 may have for example a second shape which is optimized for placement of its distal end 22 at or near the coronary sinus ostium. The anatomical or surgical function which each element of introducer system 10 is intended to spatially serve is arbitrary and may be varied according to the application at hand.

In the illustration of FIGS. 1a and 1b distal portion 17 has the predetermined shape or bias. The portion of telescoping element 16 proximal to portion 17 may be flexible or shapeless, or provided with one or more different shapes. The shape instilled into portion 17 may be created by conventional manufacturing techniques or the structure of portion 17, may be instilled into portion 17 by a shaped guide inserted into lumen 29 defined in telescoping elongate element 16, which is then later removed once telescoping elongate element 16 is implanted.

Figure 1F:
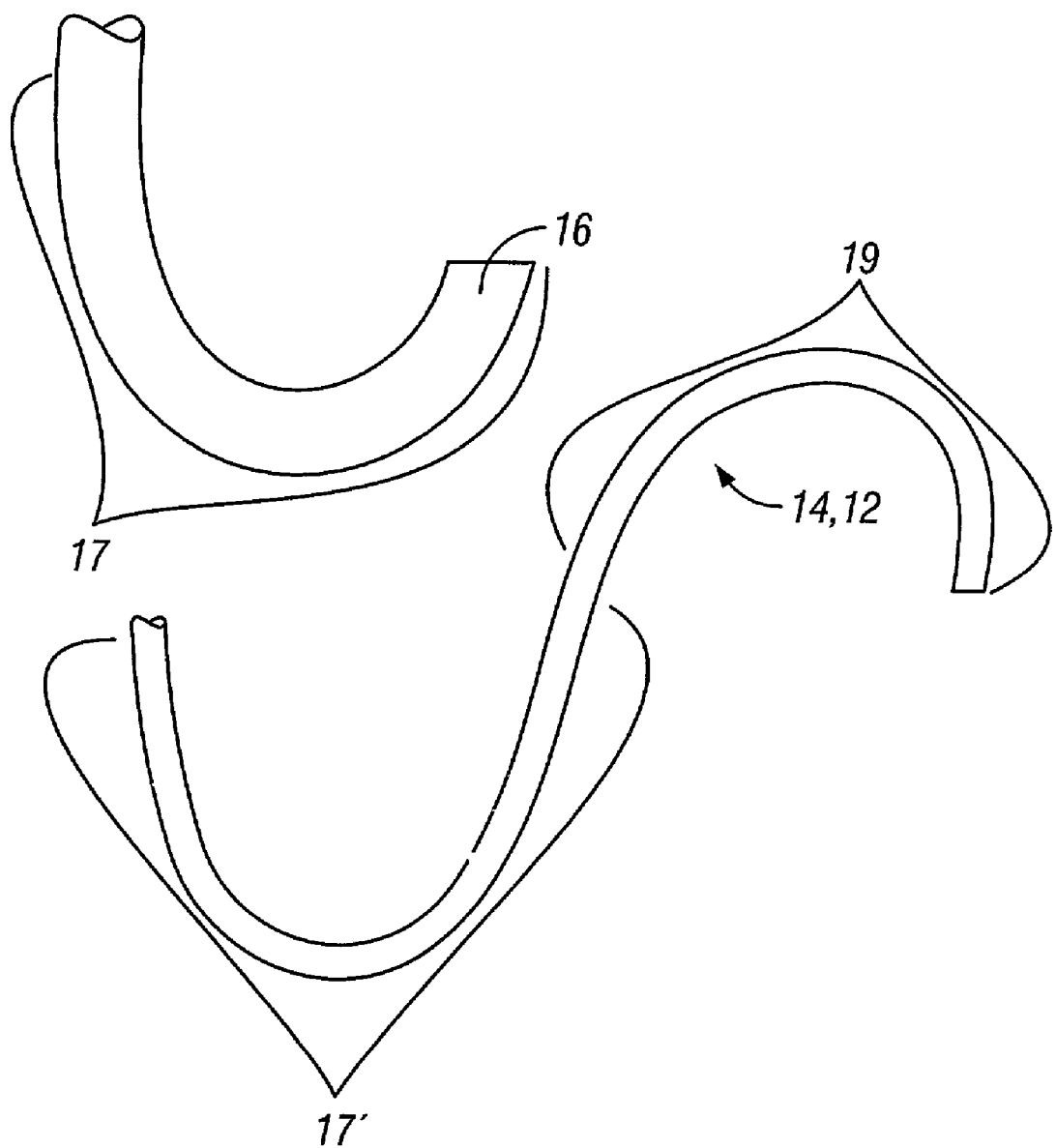
FIG. 1*f* is a side elevational view of the outer sheath and the inner sheath or core shown in a side-by-side comparison in their biased configurations.

FIG. 1f shows inner telescoping elongate element 14 and/or inner telescoping core 12 and telescoping elongate element 16 in a side-by-side comparison as might be seen if both elements were laid flatly next to each other and not telescopically nested within each other. Inner telescoping elongate element 14 and/or inner telescoping core 12 will be referenced in the alternative below as inner elongate element 12, 14. Inner elongate element 12, 14 and telescoping elongate element 16 have biased curvatures or shapes which they will assume or tend to assume if not constrained. As depicted in FIG. 1f, telescoping elongate element 16 has a first predetermined shape on distal portion 17, which is substantially matched by a first predetermined shape on distal portion 17' of inner elongate element 12, 14. On a more distal portion of inner elongate element 12, 14 from portion 17', inner telescoping elongate element 14 or inner telescoping core 12 will have a second shape or bias defined in portion 19, which is different from the shape of portion 17'. In the case of inner telescoping core 12, it may continue even further to have still a more distal portion with a third shape or bias, if desired. It is also within the scope of the invention that inner telescoping elongate element 14 may have multiple biased or shaped distal portions.

The feature of interest is that there will be some more proximal subportion of the distal portion of the elongate element 12, 14, which will be disposed within outer telescoping elongate element 16, which delivers all elements to the os of the coronary sinus, which subportion has a shape which matches that of outer elongate element 16 and which by virtue of such match automatically tends to spatially orient inner elongate element 12, 14 with outer elongate element 16, so that when inner elongate element 12, 14 is extended from outer elongate element 16, it will be oriented in space in a predetermined direction in the coronary vascular system. In general the curvatures which may be employed will be dictated by the specific application at hand, but in the illustrated embodiment outer elongate element 16 assumes the shape of the Worley catheters for delivery to the coronary sinus. Inner elongate element 12, 14 will then have a shape depending on which branch of the coronary vascular system is to be accessed.

When inner telescoping core 12 and inner telescoping elongate element 14 are disposed in portion 17 of telescoping elongate element 16 as shown in FIG. 1a, they substantially assume the shape of portion 17. The shape or bias of that portion of inner telescoping core 12 and inner telescoping elongate element 14 aligned with portion 17 in FIG. 1a may be quite differently shaped or biased.

When telescoping elongate element 14 is then extended distally from end 30 of the outer telescoping elongate element 16, inner telescoping sheath, introducer or guide 14 assumes its own shape or bias as defined in portion 19 of telescoping elongate element 14 as shown in FIG. 1c. The orientation and direction of the distal curve or tip of the inner introducer or guide will be the same as the orientation and direction of the outer guide unless the inner elongate element is manually torqued out of this orientation or the more proximal first shapes or curves of each of the inner and outer sheaths, guides or introducers are brought into alignment such as in FIG. 1d. This alignment results in the distal curve of the inner elongate element being rotated and positioned into the desired orientation and location for branch vein cannulation. Assuming for the sake of illustration that telescoping elongate element 14 has been fully extended, then the proximal portion 17' of inner elongate element 14 which is adjacent to portion 17 of outer telescoping elongate element 16, has preferably been provided with the same or similar longitudinal and or angular shape or bias as portion 17. Thus, portions 17 and 17' will now be conforming to each other when the inner elongate element is advanced or axially rotated within the outer guide to make their shapes congruently match each other. This congruent match will be mechanically favored and the most stable relative alignment of elongate element 14 and telescoping elongate element 16. Their congruent match can be manually felt by the operating physician at the proximal ends. When this congruent match is achieved, it will then rotate and fix the relative angular orientation of portion 19 of sheath, introducer, core or guide 14. If elongate element 16 is implanted into the coronary sinus and the congruent match achieved, then portion 19 will be extending in a predetermined selected orientation in three dimensional space as intended for access the desired portion of the coronary sinus branch venous system as in FIG. 1d.

In the same manner, core 12 has a distal predetermined shape or bias 21 which is assumed when core 12 is distally extended. A more proximal portion 19' of core 12 congruently matches portion 19 of elongate element 14, and an even more proximal portion 17'' of core 12 congruently matches portion 17' of elongate element 14 and portion 17 of elongate element 16. The relative angular orientations may be chosen so that when portion 19' is congruent with portion 19, portion 17'' is congruent with portions 17' and 17, or may be chosen so that the relative angular orientations of the elements are different for when portion 19' is congruent with portion 19, than when portion 17'' is congruent with portions 17' and 17. Again, the congruency of the elements is usually achieved automatically when the inner elongate element 14 is advanced through the outer guide 16, due to the more favorable mechanical axial forces on the two telescoping introducers when their curves align, and can also be felt by the physician at the proximal ends of core 12, guide 14, and elongate element 16. In each case the relative orientation of congruency is the mechanically favored and most stable relative orientation of the elements. Portions 19 and 21 may be shaped or not according to the desired access and treatment sought in the venous system.

Figure 3A:
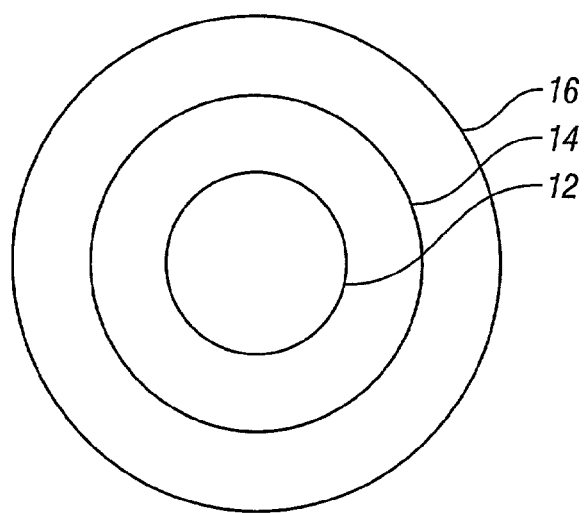
FIG. 3*a* is a radial cross-sectional view of an embodiment of the invention wherein congruent match between the elements of the introducer system is supplemented or provided by matching of the eccentric or radial profiles of the telescopic elements.

The preferred embodiment has been described in terms of congruency between different longitudinal portions of the elements. However, it is also possible to base the congruency of the elements on radial congruence. For example, as shown in FIG. 3a the cross section of the elements may each be slightly egged or oval. The tightness of the fit will be determined by the degree of eccentricity of the oval and the clearance between the lumens defined in the elements and outer diameter of the telescopic element disposed in the lumen. Although the longitudinal shape is sufficient to provide a congruent matching configuration, the addition of radial eccentricity supplements the congruency match and, in the case of one or more elements have flexible unshaped or unbiased portions, still allows for a preferred angular congruent match between the elements.

Figure 3B:
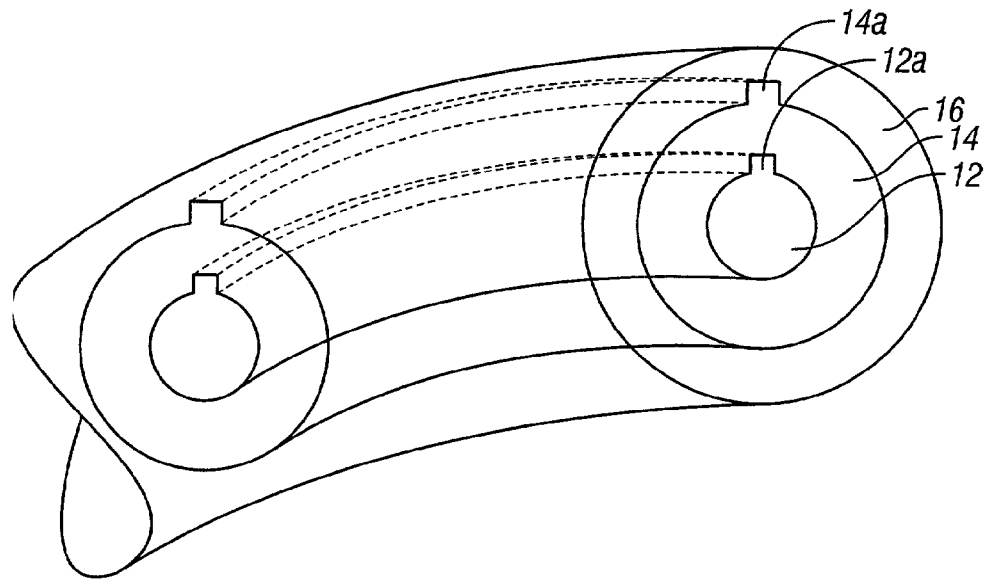
FIG. 3b is a cutaway perspective view of another embodiment of the invention where a key and keyway combination is defined in the telescopic elements to insure their angular alignment.

In the extreme the elements may have polygonal cross sections which are virtually keyed to each other, but may allow relative rotation due to the softness of material or large tolerances between them. Thus, the invention includes the use of a longitudinal tongue-and-groove combination or a detent ball-and-socket combination along portions of the elements to provide a congruent match or to enhance the proximal feel of congruent match when achieved. The keyway or detent mechanism may be placed at any position along the elongate elements, along any segment of the elements, or along their entire mutual lengths. For example, as shown in FIG. 3b a prismatic rectangular key 14a is defined on inner elongate element 14, which slidingly mates into a correspondingly shaped prismatic rectangular keyway defined in the inner surface 34 of outer elongate element 16. In the same manner a prismatic rectangular key 12a is defined on inner elongate element 12, which slidingly mates into a correspondingly shaped prismatic rectangular keyway defined in the inner surface 28 of outer elongate element 16. In this manner inner elongate elements 12 and 14, elongate elements 14 and 16, or all of them will always be angularly aligned with each other. For example, a stylet may be keyed to a pacemaker lead and thus always aligned with respect to the lead, while the delivery introducer, serving as outer elongate element 16, is freely rotatable with respect to the pacemaker lead, or has a preferred relative angular orientation to the pacemaker lead by any one of the disclosed means of the invention.

Figure 3C:
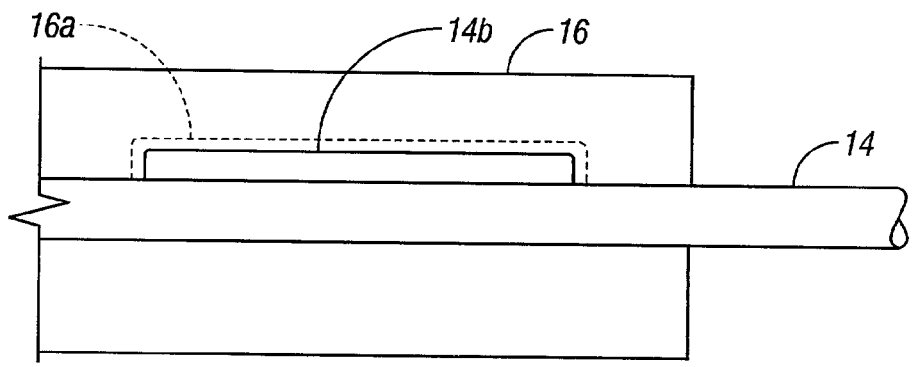
FIG. 3c is a side cross-sectional view of an embodiment where a detent mechanism is employed to insure angular alignment of the telescopic elements.
Figure 3D:
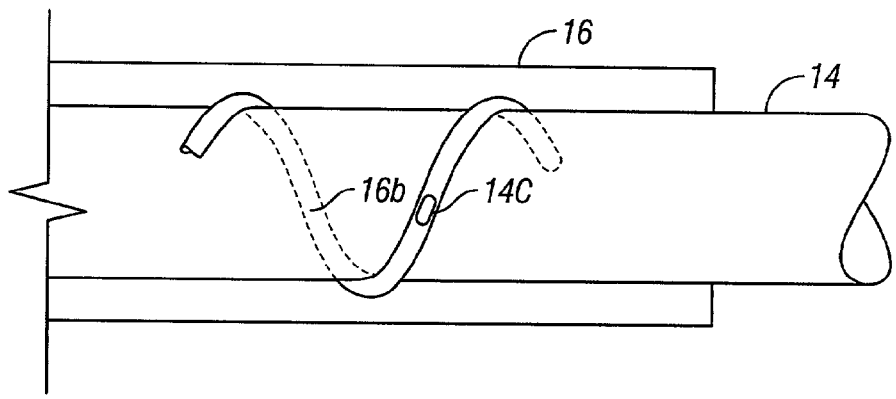
FIG. 3d is a side cross-sectional view of an embodiment where a cam follower mechanism using a helical alignment groove and cam combination is employed to insure angular alignment of the telescopic elements.

FIG. 3c illustrates a detent mechanism in which a prismatic detent pin 14b is defined on a proximal portion of inner elongate element 14 which snap fits or locks into a detent cavity 16b defined in inner surface 34 of outer elongate element 16, when inner elongate element 14 is extended from outer elongate element 16.

It is further contemplated that follower pin 14c may act as a cam follower and snap into a 360° helical groove 16b defined in inner surface 34 of outer elongate element 16, so that when inner elongate element 14 is extended from outer elongate element 16 by the designed amount, follower pin 14c will necessarily cross the helical groove 16b, snap into it and become captured by it, and the rotate inner elongate element 14 so that it has the properly angular orientation with respect to outer elongate element 16 when pin 14c reaches the distal end of the helical groove 16b.

The result is that the emerging inner elongate element 12, 14 has a predetermined angular orientation with respect to the outer elongate element 16. If the outer elongate element 16 is steered to the coronary ostium and positioned correctly, then the physician can be assured that as the inner elongate element 12, 14 has an angular orientation relative to the venous system that the second shape defined into at least the distal portion of inner elongate element 12, 14 will be assumed for that portion extended from outer elongate element 16 and will be properly placed into the venous system.

Returning now to the description of the elements of introducer system 10 in FIGS. 1a and 1b, it is to be understood that core 12 may be made of either a nonreinforced plastic extrusion, solid or hollow or of a reinforced material such as a braid and may be of a single durometer or of multiple durometers. In either case, core 12 is torqueable, which means that its proximal end 18 can be rotated by the physician and its distal end 20 will rotate by a corresponding amount. In other words, while core 12 may be laterally flexible, it is torsionally stiff. In general, inner elongate element 14 and outer elongate element 16 will be both laterally and torsionally flexible. In one embodiment, however, as described below, core 12 may be omitted and inner or outer guide or introducer 14 will then be made to be torsionally stiff.

In the embodiment where inner elongate element 14 is unreinforced and hence not torqueable, it is used with telescopic core 12, which is provided with a structure or reinforcement which renders it torqueable. The frictional coupling or binding between the inner surface of a lumen 28 defined in elongate element 14 and the outer surface of core 12 allows the distal end 22 of inner elongate element 14 to be rotated when core 12 is proximally rotated. The alignment of the identical first and second shapes of the core 12 and non-torqueable elongate element 14 also allow for uniform rotation of the unit as a whole simply by rotating the core 12. In the preferred embodiment core 12 includes a braided reinforcement of fibers in or on its body running along its length, which reinforcement renders it torsionally stiff while leaving it radially flexible, even when it has a diameter which is too small to render core 12 torsionally stiff simply by virtue of its size and unreinforced material constituency. In other words, but for the reinforcement core 12 would not be torqueable. Therefore, it is within the scope of the invention that the invention contemplates the combination of a nontorqueable sheath, introducer, guide or catheter in combination with a structurally reinforced core 12 which is torqueable and which core 12 is used to render the combination torqueable.

Inner elongate element 14 is preferably peelable, longitudinally torn apart, or in the case of a reinforced elongate element 14, it is sliceable, in which case the elongate element may be opened longitudinally. The material of which inner elongate element 14 is made may be of such a nature that it tears preferentially along a longitudinal line, or it may be weakened by a defined longitudinal indentation or a longitudinal region of softer or weakened material as is well known to the art. The particular manner by which inner elongate element 14 can be separated is not material to the invention as long as the elongate element can be removed or peeled off of the pacemaker lead or other device as well as any proximal connectors or fittings that might be in place after the pacemaker lead (not shown) or medical device is implanted as described below. Any structure which will permit the division of the guiding inner and outer elongate element 14 into two separate longitudinal halves is within the scope of the invention. In one preferred embodiment, the guiding inner elongate element 14 contains a pair of mechanically formed, longitudinally extending zones of reduced thickness defined by internally scored, longitudinally shallow grooves or indentations running throughout the length of the inner elongate element 14. These mechanically formed, reduced thickness zones permit the guiding inner elongate element 14 to be "split" following use. Alternatively, if the lumen 28 of inner elongate element 14 is sufficiently large and the size of the diameter of the medical device passing through the guiding inner elongate element 14 is not larger than lumen 28 of inner elongate element 14, it is not necessary that the guiding inner or outer elongate element 14 be splittable.

The same feature of longitudinal separability is also true for the outer guide 16. In the illustrated embodiment of FIGS. 1a and 1b inner elongate element 14 employs or is used in combination with core 12, which made of a material that allows for torque control. In the embodiment where inner elongate element 14 is a guide, i.e. made of a reinforced material, then no inner core 12 is required because inner elongate element 14 itself would be torqueable. In this latter embodiment inner elongate element 14 would then likely need to be sliced away.

In prior art arterial telescopic catheter systems, such as shown in U.S. Pat. No. 4,616,652, the prior art system requires the telescoping inner tube to track over a wire. This is not the case with telescopic catheter 10 of the invention. While inner elongate element 14 may track over a wire, it is specifically designed, by virtue of its unique biased shapes and soft flexible distal end described below to cannulate the branch coronary veins without the aid of any wire system. In the embodiment of FIGS. 1a and 1b the shaped or biased, but non-reinforced elongate element 14 will not be torsionally stiff, or at least not so torsionally stiff as to be satisfactorily steered by proximal rotations. Such a non-reinforced elongate element 14 incorporates a coaxially disposed core 12, which is torsionally stiff and allows for steering of the combined sheath/core unit 12, 14. The core 12 is what allows the non-reinforced elongate element 14 to be torqued or controllably rotated by proximal rotations of the sheath. There is sufficient clearance in a central lumen 28 defined in elongate element 14 to allow core 12 to be longitudinally displaced within elongate element 14. However, when elongate element 14 is allowed to assume its intended biased curvatures, as when distal end 30 of flexible outer elongate element 16 is placed at the ostium of the coronary sinus and inner elongate element 14 is advanced into the coronary venous system, there is sufficient friction or binding between core 12 and lumen 28 of inner elongate element 14, such that inner elongate element 14 and core 12 rotate together as core 12 is proximally rotated. The distal curvature of the telescoping inner elongate element 14 and the frictional coupling or binding between inner elongate element 14 and inner core 12 and the proximal locking of the core 12 to elongate element 14 are sufficient to permit reliable rotation of the two as a unit. First the outer elongate element 16 is placed then the inner telescoping sheath or guide 14 is next placed. Thus, in the embodiment of FIGS. 1a and 1b the angulation or bias needed to navigate the coronary venous system is provided in the structure of inner elongate element 14, while the means of rotation inner elongate element 14, so that it can be steered as desired in the coronary venous system, is provided by the relationship between core 12 and inner elongate element 14 as well as by the alignment of the congruent first shapes of the inner and outer introducers 14, 16 and core 12.

Alternatively, in the embodiment of FIG. 2 elongate element 14 is reinforced with an internal braid or torsionally stiff layer 32 in or on elongate element 14, and no core 12 is used. Reinforced elongate element 14 is also provided with the shaped bias through portion 17 which shaped bias is needed to optimally navigate elongate element 14 into the coronary sinus venous system. Because of its torsional stiffness, guide 14 can be proximally rotated within lumen 34 in guide 16 with distal end 22 tracking the proximal rotations.

In FIGS. 1a and 1b core 12 extends out a short distance past distal end 22 of elongate element 14 and has a soft radioopaque tip 24 for ease of fluoroscopic visualization. Core 12 provides both longitudinal and axial reinforcement as well as containing a central longitudinal lumen 26 for a wire and contrast injection. The inner telescoping elongate element 14 with an integral core 12 can be placed through the outer elongate element 16 and advanced longitudinally. With the alignment of the first shapes of the inner and outer telescoping elements 14 and 16, and manual torqueing along with intermittent small amounts of contrast agent injections, visualization of the desired branch vein branch is accomplished. Once the desired venous branch is cannulated by the protruding core 12, inner elongate element 14 is advanced over and past core 12 into the proximal portion of the desired vein. At this point core 12 is removed and pulled out of both the inner telescoping elongate element 14 and the outer guide 16. A wire (not shown) can the be placed if desired for an over-the-wire pacemaker lead or the pacemaker lead can be advanced through telescoping elongate element 14 directly into the target vein without the use of a wire.

Of course if telescoping elongate element 14 is reinforced it will not require a core 12, but would act as a guide. It would then need to be sliced away once the pacemaker lead is in the desired location. The outer elongate element 16 is preferably sliced or peeled away after the telescoping elongate element 14 has been removed, but may be removed first. The outer elongate element is generally placed in the coronary sinus first and the inner telescoping elongate element is placed second.

Figures 4, 5:
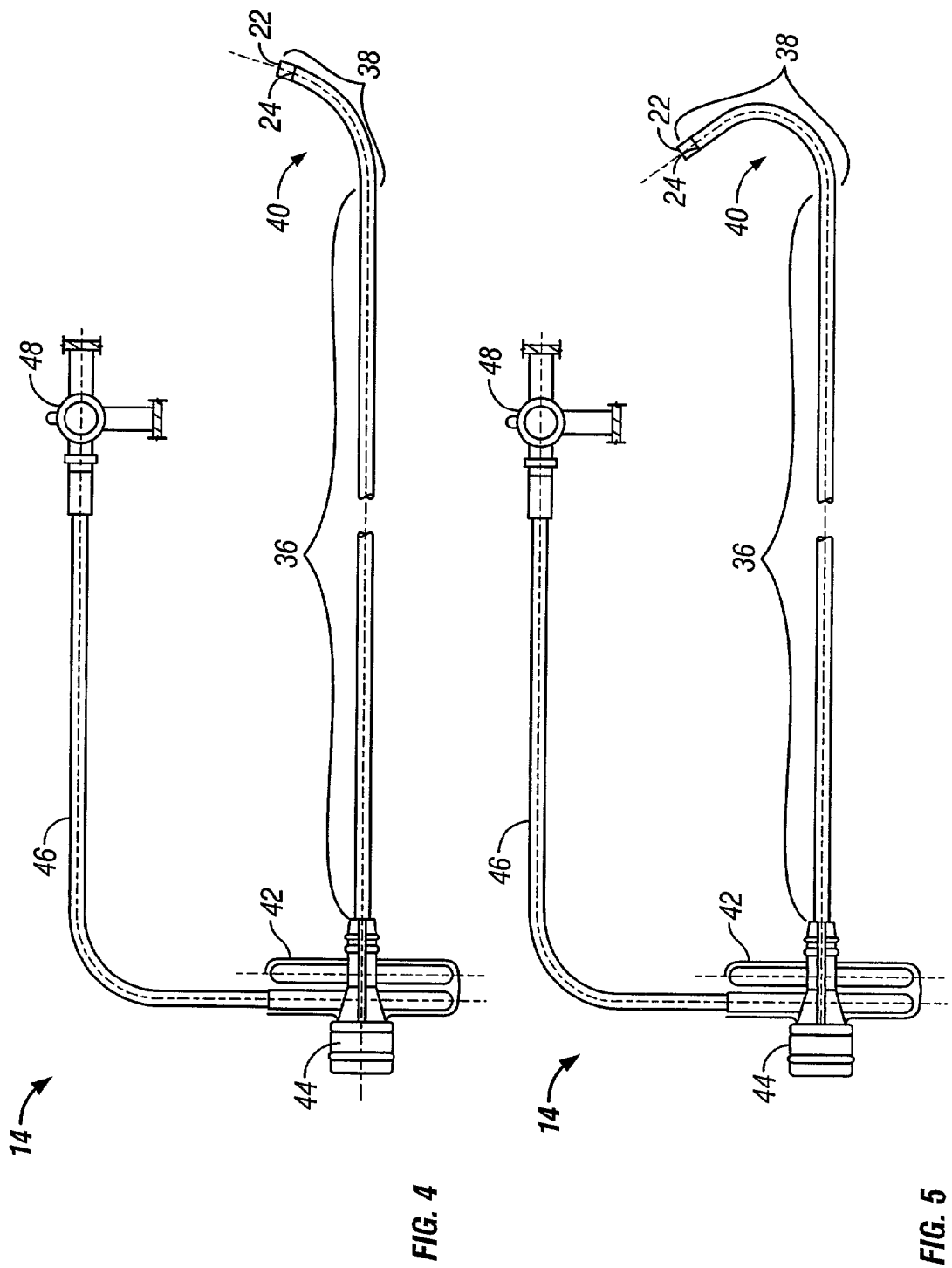
FIG. 4 is a plan view of another embodiment of an introducer formed according to the invention.
FIG. 5 is a plan view of still another embodiment of an introducer formed according to the invention.

FIG. 4 is a plan elevational side view of one embodiment of splittable inner elongate element 14 of the invention. A proximal handle 42 is connected to a hub 44. A flexible sidearm tube 46 is communicated to hub 44 and is distally terminated with a hemostatic valve 48 through which contrast agent and other fluids may be injected into lumen 26 of inner elongate element 14. Inner elongate element 14 may lie in a single plane, such as the plane of FIG. 4. However, it is to be expressly understood that portions of inner elongate element 14 may be biased above or below the plane of FIG. 4 to provide an arbitrarily, three dimensionally shaped elongate element 14. Portion 36 is defined as the proximal portion of inner elongate element 14 and is prebiased into the first shape but may be unbiased, flexible section of inner elongate element 14 leading from the percutaneous introduction point into the left cephalic, auxiliary or subclavian veins and through the vasculature leading toward the right atrium and coronary sinus of the heart.

A biased portion 38, distal second shape, of inner elongate element 14 forms the distal portion of inner elongate element 14, and is either integral with or may be separately fabricated from portion 36. While still being flexible, portion 38 is biased to have a memory so that when the vasculature permits, it tends to assume a prebiased shape as seen in FIG. 4 and described in more detail below. On the other hand, the bias is not so stiff that portion 38 is not easily conformed to the vasculature without risk of injury or trauma.

In general terms, portion 38 has an arcuate bias to form a modified circular or general purpose curvature so that the lateral distance 40 measuring the lateral deflection from the straight line of portion 36 as seen in FIG. 4 is in one embodiment approximately 1.16 inch. Its radius of curvature is approximately 1.31 inch. Inner elongate element 14 in this embodiment has a total length of 22.87 inches, and a 7 French inner diameter. However, lateral distance 40 may vary within a range of the illustrated embodiment, namely in a range of 30 to 65 cm.

The distal end 22 is straightened or slightly straightened to at least have less curvature than the remainder of portion 38 or a very low curvature, if any. A perpendicular line to the longitudinal axis of inner elongate element 14 at distal end 22 makes an angle with respect to the extended straight line of portion 36 as shown in FIG. 4 of approximately 23°.

Similarly, in a second embodiment of FIG. 5, what is shown is a plan elevational side view of one embodiment of splittable inner elongate element 14 of the invention. Again a proximal handle 42 is connected to a hub 44. A flexible sidearm tube 46 is communicated to hub 44 and is distally terminated with a hemostatic 48 through which contrast agent and other fluids may be injected into lumen 26 of inner elongate element 14. Inner elongate element 14 may lie in a single plane, such as the plane of FIG. 5. However, it is to be expressly understood that portions of inner elongate element 14 may be biased above or below the plane of FIG. 5 to provide an arbitrarily, three dimensionally shaped elongate element 14. Portion 36 is the defined as the proximal portion of inner elongate element 14 and is a generally unbiased, flexible section of inner elongate element 14 leading from the percutaneous introduction point into the left cephalic, auxiliary or subclavian veins and through the vasculature leading toward the atrium and coronary sinus of the heart.

A biased portion 38, distal second shape, of inner elongate element 14 forms the distal portion of inner elongate element 14, and is either integral with or may be separately fabricated from portion 36. While still being flexible, portion 38 is biased to have a memory so that when the vasculature permits, it tends to assume a prebiased shape as seen in FIG. 5 and described in more detail below. On the other hand, the bias is not so stiff that portion 38 is not easily conformed to the vasculature without risk of injury or trauma.

In general terms, portion 38 has an arcuate bias to form a modified hooked or acute curvature so that the lateral distance 40 measuring the lateral deflection from the straight line of portion 36 as seen in FIG. 5 is in this embodiment approximately 1.12 inch. The radius of curvature of portion 38 is approximately 0.49 inch. Inner elongate element 14 in this embodiment has a total length of 22.87 inches and a 7 French inner diameter. However, lateral distance 40 may vary within a range of the illustrated embodiment, namely in a range of 35 to 65 cm.

The distal end 22 is again straightened or slightly straightened to at least have less curvature than the remainder of portion 38 or a very low curvature, if any. In the embodiment of FIG. 5 the straightened distal segment of portion 38 is approximately 0.40 inch long. The longitudinal axis of inner elongate element 14 at distal end 22 makes an inner angle with respect to the straight line of portion 36 as shown in FIG. 5 of approximately 58°.

Figures 6, 7:
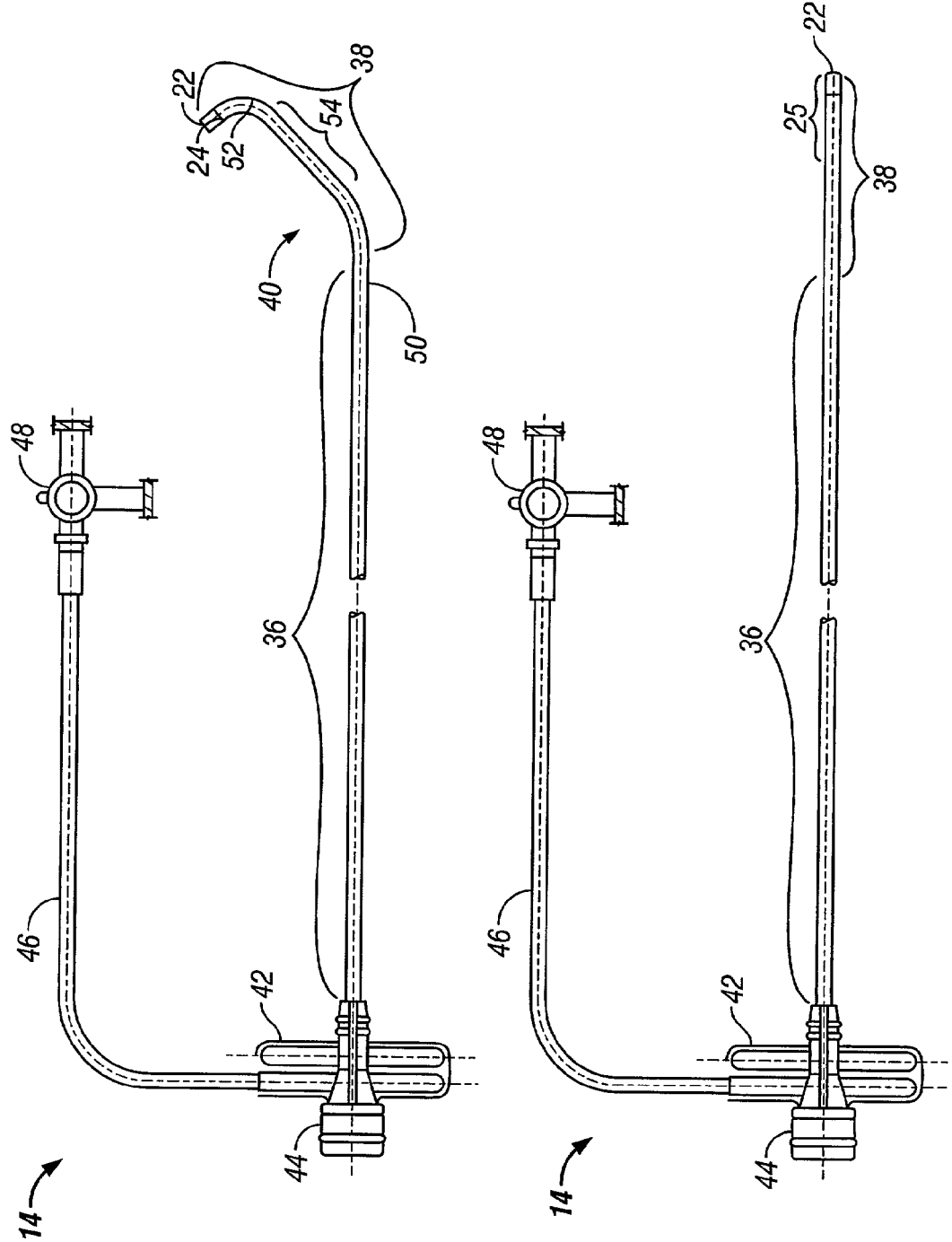
FIG. 6 is a plan view of yet another embodiment of an introducer formed according to the invention.
FIG. 7 is a plan view of an embodiment of the invention where the distal portion of the introducer is straight.

Still further, in a third embodiment of FIG. 6, what is shown is a plan elevational side view of one embodiment of splittable inner elongate element 14 of the invention. Again a proximal handle 42 is connected to a hub 44. A flexible sidearm tube 46 is communicated to hub 44 and is distally terminated with a hemostatic valve 48 through which contrast agent and other fluids may be injected into lumen 26 of inner elongate element 14. Inner elongate element 14 may lie in a single plane, such as the plane of FIG. 6. However, it is to be expressly understood that portions of inner elongate element 14 may be biased above or below the plane of FIG. 6 to provide an arbitrarily, three dimensionally shaped elongate element 14. Portion 36 is the defined as the proximal portion of inner elongate element 14, proximal first shape, and is a generally prebiased but may be unbiased, flexible section of inner elongate element 14 leading from the percutaneous introduction point into the left auxiliary subclavian vein and through the vasculature leading toward the atrium of the heart.

A biased portion 38 of inner elongate element 14 forms the distal portion of inner elongate element 14, and is either integral with or may be separately fabricated from portion 36. While still being flexible, portion 38 is biased to have a memory so that when the vasculature permits, it tends to assume a prebiased shape as seen in FIG. 6 and described in more detail below. On the other hand, the bias is not so stiff that portion 38 is not easily conformed to the vasculature without risk of injury or trauma.

In general terms, portion 38 has an arcuate bias to form a modified flattened some portion, so that the lateral distance 40 measuring the lateral deflection from the straight line of portion 36 as seen in FIG. 6 is in this embodiment approximately 1.47 inch. The more proximal radius of curvature 50 of portion 38 is approximately 1.06 inch. Distal to curvature 50 is a straight portion 54 of length 0.88 inch. Straight portion 54 is then followed by a second and more distal radius of curvature 52 of portion 38, Which is approximately 0.26 inch.

Inner elongate element 14 in this embodiment has a total length of 22.87 inches and a 7 French inner diameter. However, lateral distance 40 may vary within a range of the illustrated embodiment, namely in a range of 35 to 65 cm.

The distal end 22 is again straightened or slightly straightened to at least have less curvature than the remainder of portion 38 or a very low curvature, if any. The longitudinal axis of inner elongate element 14 at distal end 22 makes an outer angle with respect to the extended straight line of portion 36 as shown in FIG. 6 of approximately 47°.

FIG. 7 is a plan view of another embodiment of the invention similar to that of FIGS. 4-6 except that distal portion 38 is straight instead of the various curved shapes described above. Thus, distal portion 38 is essentially a continuation of straight proximal portion 36.

Inner elongate element 14 may be made of any biocompatible material suitable for use in humans which has a memory or permits distortion from and substantial return to the desired three dimensional shape, such as polyethylene or polyurethane. As is conventional the distal tip 22 of the guiding inner elongate element 14 may be made of a more pliable, more compressible material, than the remaining length of the coronary sinus guiding inner elongate element 14 to prevent damage to the vasculature and the coronary sinus when in use.

For the purpose of illustration and not limitation, the internal diameter of the guiding inner sheath, core, guide or introducer 14 may vary from about 3 to about 16 French (1 French equals ⅓ of a millimeter). The precurved guiding inner elongate element 14 of the invention may also be multi-lumened. According to conventional design principles, the structure of inner elongate element 14 may be modified to permit the presence of an inflatable balloon 25 near or at its distal tip or electrodes for sensing or ablation. Balloon 25 is fabricated using conventional methods and designs and is communicated with a lumen defined within element 14 for the purposes of inflation and deflation with an exteriorly supplied fluid.

Variations in size and shape of the guiding inner elongate element 14 are intended to encompass pediatric uses for the guiding introducer of the present invention, although the preferred uses are in adult human hearts. It is well recognized that pediatric uses may require reductions in size of the various portions of the inner elongate element 14, in particular shortening the first portion 36, with a proportional reduction in the height, arc and length of curved distal portion 38 of the guiding inner elongate element 14, which may extend the lower limits of the specific ranges of the above parameters from those explicitly recited below. In addition, variations in size or shape are also intended to encompass specialized situations that sometimes occur in patients with enlarged or rotated hearts.

The guiding inner elongate element 14 can be used to introduce a number of different types of medical instruments into the body through its lumen including a permanent or temporary pacemaker lead, a defibrillator lead, ablation or sensing catheters or any such medical devices that will find use if placed within the coronary sinus. These other uses are well known in the industry and are within the contemplation of the present invention.

Figure 8:
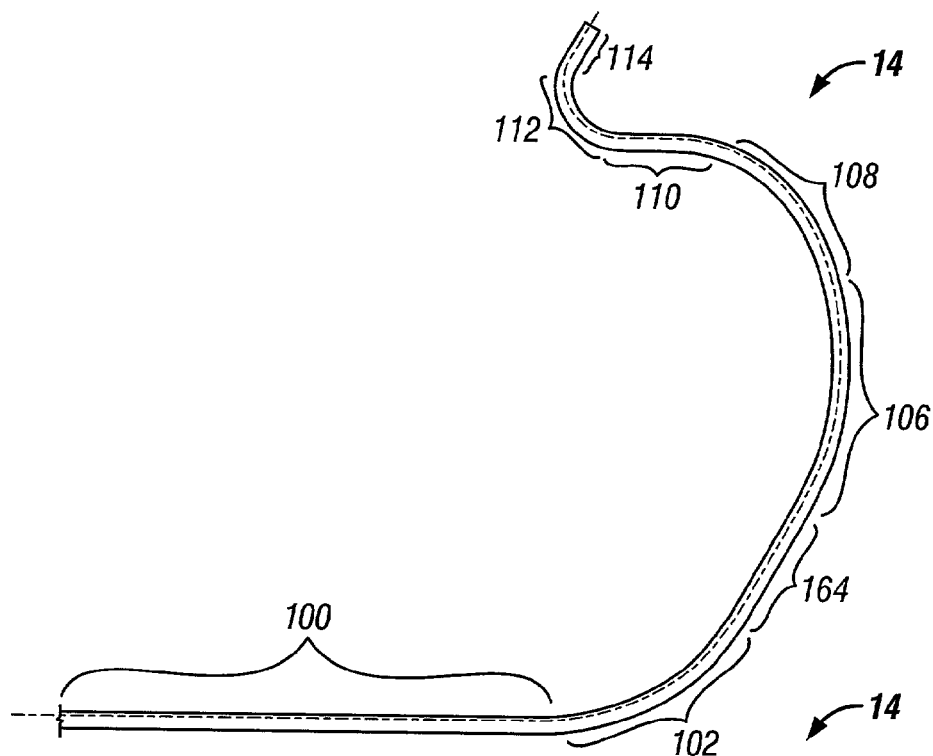
FIG. 8 is a plan side view of a first embodiment of the inner elongate element.

FIG. 8 is a side plan view of an embodiment of sheath, core, introducer, guide or, more generally, an elongate element 14 formed into a shape of what is termed an "elephant curve" shown in a hockey stick version. Elongate element 14 may comprise an inner sheath fitted with a hub, sidearm and valve (not shown), and/or may comprise a core which is telescopically disposed into a sheath, introducer or guide in which case a proximal hub may or may not be provide, and in which case a sidearm and valve are not included. A flexible, straight or unbiased portion 100 transitions to biased compound curved distal portions of element 14. A first portion 102 with a radius of curvature of approximately 2.08 inch transistions to a 1.17 inch long straight portion 104, such that portions 100 and 104 make an angle of 59° with respect to each other. A second curved portion 106 with a radius of curvature of approximately 2.83 inch follows portion 104 and subtends an angle of 57°. A third curved portion 108 follows portion 106 and has a radius of curvature of approximately 1.33 inch and subtends an angle of 64°. A short straight portion 110 of length 0.68 inch then connects portion 108 to an oppositely curved portion 112 having a radius of curvature of approximately 0.49 inch and subtending an angle of 122°. Finally, sheath, introducer or guide 14 of FIG. 8 terminates in a short straight portion 114 of 0.40 inch length. Thus, while the compound curve of FIG. 8 is comprised of a plurality of curvatures, it can be viewed as a more proximal compound curve comprised of portions 102, 104 and 106, and a distal compound curve comprised of portions 108, 110, 112 and 114. Outer sheath, introducer or guide 16 may thus have a distal portion provided with a compound curve of comprised of or congruent with portions 102, 104 and 106. Inner sheath, introducer or guide 14 of FIG. 8 would then have a tendency to align the two matching portions so that the distal compound curve comprised of portions 108, 110, 112 and 114 extend from outer sheath, introducer or guide 16 into the venous system in the intended spatial orientation.

Figure 9:
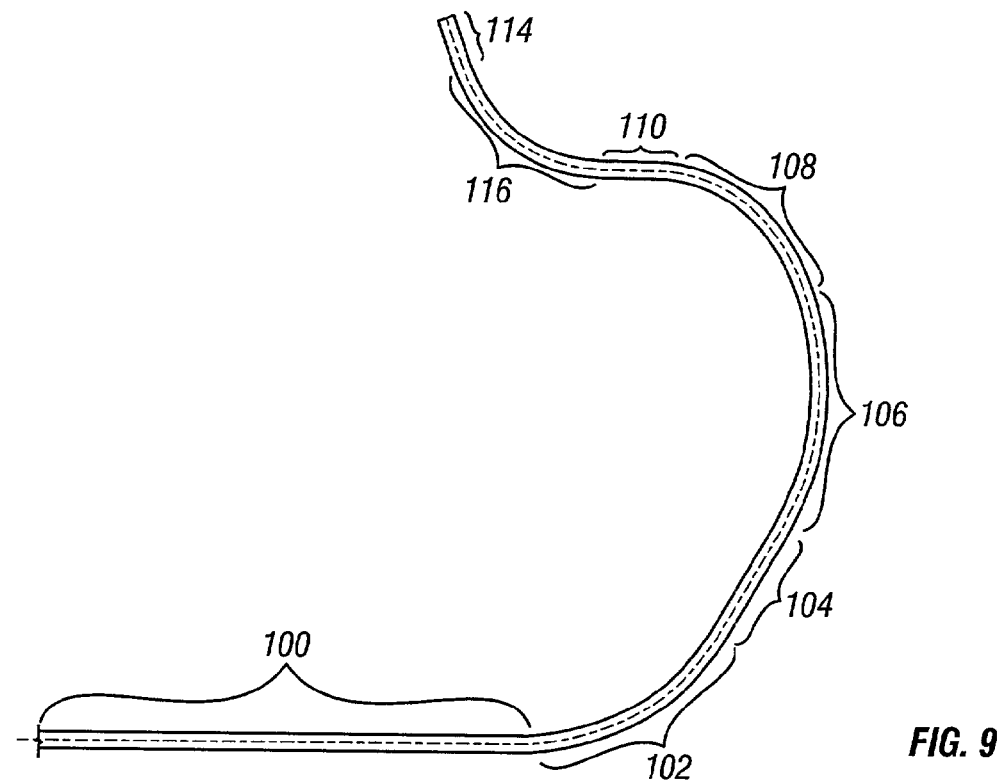
FIG. 9 is a plan side view of a second embodiment of the inner elongate element.

Another embodiment of elongate element 14 is shown in side plan view in FIG. 9. Each of the portions of the embodiment of FIG. 8 are reproduced in the embodiment of FIG. 9 except that portion 112 of FIG. 8 has been replaced by portion 116 of FIG. 9, which is a curved section with a radius of curvature of approximately 1.31 inch and subtending an angle of 67°. This shape is called a multiple purpose version of the elephant curve.

Figure 10:
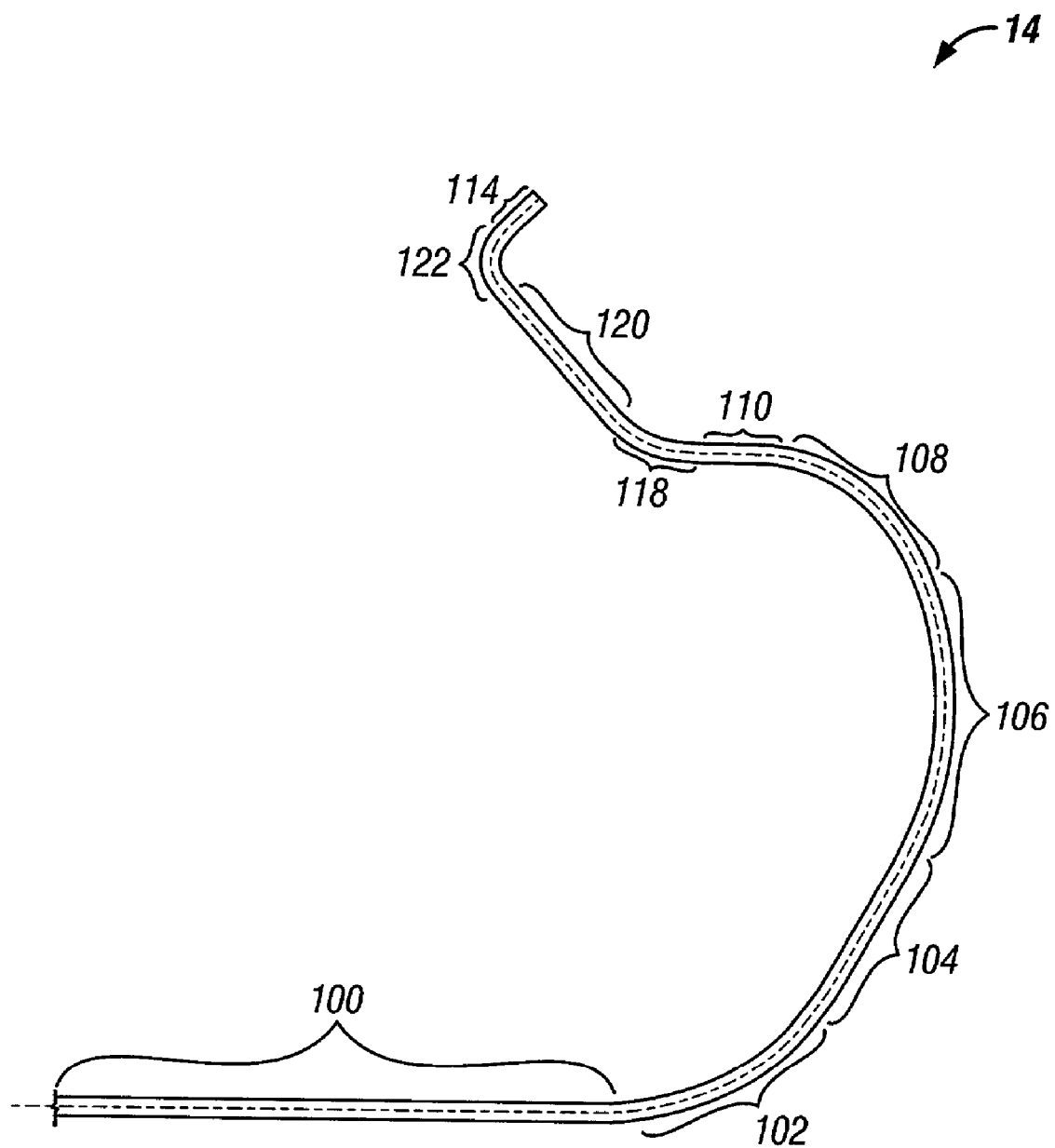
FIG. 10 is a plan side view of a third embodiment of the inner elongate element.

Still another embodiment of elongate element 14 is shown in side plan view in FIG. 10. Each of the portions of the embodiment of FIG. 8 are reproduced in the embodiment of FIG. 10 except that portion 112 of FIG. 8 has been replaced by portions 118, 120 and 122 of FIG. 10. Portion 118 is a curved section with an opposite radius of curvature of approximately 1.06 inch and subtending an angle of 43°. Portion 120 is a straight portion with a length of approximately 0.88 inch. Portion 118 is a curved section with an opposite radius of curvature of approximately 0.26 inch and subtending an angle of 90°. This shape is called the hook version of the elephant curve.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims.

For example, features of this guiding inner elongate element 14 include its unique shape, but may also incorporate a sliceable, peelable or splittable structure, increased stiffness to minimize compression when positioned in tight bends, radioopaque tip sections or markers, balloons and vents according to conventional design principles.

While the illustrated embodiment has described an inner sheath, guide or introducer within an outer sheath, guide or introducer, it must also be understood that the invention also expressly contemplates a stylet with first-shape and second-shape portions used with a pacemaker lead, both of which are then delivered as a unit through an introducer with a first-shape portion. The stylet/pacemaker lead combination is used as a unit to steer or rotate the introducer into proper position. The stylet/pacemaker lead combination is then extended from the introducer into the venous system, assuming the second shape in the venous system. Once the stylet/pacemaker lead properly cannulates the venous system, the stylet is removed and then the pacemaker lead is implanted.

Notwithstanding the fact that the elements of a claim are set forth below in a certain combination, it must be expressly understood that the invention includes other combinations of fewer, more or different elements, which are disclosed in above even when not initially claimed in such combinations.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

We claim:

1. A telescopic introducer apparatus comprising:
   an outer elongate element; and
   an inner elongate element having a preferred relative orientation with respect to the outer elongate element, the inner elongate element being telescopically disposed in the outer elongate element, the outer and inner elements including means for rotationally coupling the outer and inner elements with respect to the other to render the outer and inner elements substantially rotatable together when the inner elongate element is distally extended from the outer element.

2. The introducer apparatus of claim 1 where:
   the outer elongate element has a first shape or bias along a first-shape portion; and
   the inner elongate element has a second shape or bias on its distal portion and has the first shape or bias on a more proximal first-shape portion, the outer and inner elements being relatively, angularly orientable with respect to each other, such that when the inner elongate element is distally extended from the outer element, the preferred angular orientation between the inner and outer elements is achieved, which angular orientation is congruent when there is at least partial alignment between the first-shape portion of the outer elongate element and the first-shape portion of the inner elongate element.

3. The telescopic introducer apparatus of claim 2 wherein the alignment between the first-shape portion of the outer elongate element and the more proximal first-shape portion of the inner elongate element comprises an alignment of a longitudinal shape or bias.

4. The telescopic introducer apparatus of claim 3 wherein the alignment between the first-shape portion of the outer elongate element and the more proximal first-shape portion of the inner elongate element also comprises an alignment of a radial cross-sectional shape.

5. The telescopic introducer apparatus of claim 2 wherein the alignment between the first-shape portion of the outer elongate element and the more proximal first-shape portion of the inner elongate element comprises an alignment of a radial cross-sectional shape.

6. The telescopic introducer apparatus of claim 2 further comprising means for rotating a distal end of the inner elongate element from a proximal end of the inner elongate element so that the inner elongate element is steerable.

7. The telescopic introducer apparatus of claim 6 where the means for rotating a distal end of the inner elongate element from a proximal end of the inner elongate element comprises a torsionally stiff core, and wherein the inner elongate element is torsionally flexible.

8. The telescopic introducer apparatus of claim 7 wherein the inner elongate element is unreinforced.

9. The telescopic introducer apparatus of claim 6 where the means for rotating a distal end of the inner elongate element from a proximal end of the inner elongate element comprises means for rendering the inner elongate element torsionally stiff.

10. The telescopic introducer apparatus of claim 2 where the inner elongate element has at least one longitudinal lumen defined therethrough adapted for injection of a fluid.

11. The telescopic introducer apparatus of claim 10 further comprising a proximal sidearm communicated to the at least one longitudinal lumen and a hemostatic valve coupled to and terminating the sidearm.

12. The telescopic introducer apparatus of claim 2 where the inner elongate element has at least one longitudinal lumen defined therethrough adapted for disposition of a guide wire therethrough.

13. The telescopic introducer apparatus of claim 2 where the inner elongate element comprises a proximal flexible unbiased portion and a distal precurved portion, which has a curvature for optimally steering the inner elongate element into the coronary sinus venous system of the heart.

14. The telescopic introducer apparatus of claim 13 wherein the distal precurved portion has a single radius of curvature and a distal most straight portion.

15. The telescopic introducer apparatus of claim 14 wherein the inner elongate element has a longitudinal axis and the single radius of curvature and relative length of the distal precurved portion are such that an open curve is obtained, an open curve being defined as having an angle between the direction of the longitudinal axis of the proximal portion of the inner elongate element where it joins the precurved portion and the direction of the longitudinal axis at a distal end of the precurved portion of the inner elongate element of more than 90°.

16. The telescopic introducer apparatus of claim 14 wherein the inner elongate element as a longitudinal axis and the single radius of curvature and relative length of the distal precurved portion are such that a closed curve is obtained, a closed curve being defined as having an angle between the direction of the longitudinal axis of the proximal portion of the inner elongate element where it joins the precurved portion and the direction of the longitudinal axis at a distal end of the precurved portion of the inner elongate element of less than 90°.

17. The telescopic introducer apparatus of claim 13 where the distal precurved portion of the inner elongate element comprises two curved subportions and a straight subportion therebetween of form a flattened hook.

18. The telescopic introducer apparatus of claim 17 where the two curved subportions comprise a proximal curved subportion having a radius of curvature of a first magnitude and a distal curved subportion having a radius of curvature of a second magnitude less than the first magnitude.

19. The telescopic introducer apparatus of claim 18 where the radius of curvature of the first magnitude is approximately 1 inch and where the radius of curvature of the second magnitude is approximately 0.2 to 0.3 inch.

20. The telescopic introducer apparatus of claim 2 where the outer elongate element is longitudinally openable or separable.

21. The telescopic introducer apparatus of claim 2 where the inner elongate element is longitudinally openable or separable.

22. The telescopic introducer apparatus of claim 2 where the outer and inner elements are both longitudinally openable or separable.

23. The telescopic introducer apparatus of claim 2 further comprising a proximal sidearm communicated to the at least one longitudinal lumen and a hemostatic valve coupled to and terminating the sidearm.

24. The introducer apparatus of claim 1 where the means for orienting the outer elongate element with respect to the inner elongate element comprises a key defined on one the outer or inner elongate elements and a corresponding keyway defined in the other one of the outer or inner elongate elements.

25. A telescopic introducer system for use in the coronary sinus venous system comprising:
an outer elongate element having a longitudinal lumen defined therein and having a bias along a first-shape portion;
a nontorqueable inner elongate element having a longitudinal lumen defined therein and having a first bias along a first-shaped portion, and a second bias along a second-shaped portion, the inner elongate element being telescopically disposed within the outer elongate element; and
an elongate, telescopic core having the second bias on its distal portion and having the first bias on a more proximal portion, the core being telescopically disposed in the lumen of the inner elongate element, the core being structurally reinforced so that it is torsionally stiff while remaining radially flexible,
wherein the inner elongate element and the core in combination are relatively rotatable as a unit with respect to the outer elongate element, and when the inner elongate element along with the core are distally extended from the outer elongate element to position first bias of first shaped portion of the inner elongate element and the first bias of the more proximal portion of the core congruently with the first-shaped portion of the outer elongate element to rotationally couple the outer elongate element with the combination of the core and inner elongate element to render the outer elongate element, the core and inner elongate element rotatable as a unit.

26. The telescopic introducer system of claim 25 where the core is adapted to rotationally couple with an inner elongate element and when in a congruent match with the inner elongate element shape or curve, the distal end of the inner elongate element being rotated when a proximal end of the core is rotated.

27. The telescopic introducer of claim 25 where the core is reinforced by a braid.

28. A telescopic introducer apparatus comprising:
an outer elongate element having a predetermined biased shape in a proximal portion of the outer elongate element; and
an inner elongate element telescopically disposed in the outer elongate element,
the inner elongate element having the predetermined biased shape in a proximal portion of the inner elongate element, the outer and inner elongate elements capable of being rotatably coupled with each other when the inner elongate element is extended distally from the outer elongate element into a deployment position and the predetermined biased shapes of the inner and outer elongate elements are congruently aligned with each other, thereby rendering the outer and inner elongate elements substantially rotatable together.

29. A telescopic introducer apparatus comprising:
an outer elongate element; and
an inner elongate element,
where the outer elongate element and inner elongate element each have corresponding proximal shapes, and when the inner elongate element is telescopically and distally extended from the outer elongate element into a deployment position, the corresponding proximal shapes of the inner and outer elongate elements couple with each other to limit relative rotation of the inner and outer elongate elements with respect to each other.

* * * * *